US011752320B2

(12) United States Patent
Garrigue et al.

(10) Patent No.: US 11,752,320 B2
(45) Date of Patent: Sep. 12, 2023

(54) ASSEMBLY FOR FITTING/REMOVING A HEART PUMP

(71) Applicant: FINEHEART, Pessac (FR)

(72) Inventors: Stéphane Garrigue, Begles (FR); Arnaud Mascarell, Montbazon (FR)

(73) Assignee: FINEHEART, Pessac (FR)

( * ) Notice: Subject to any disclaimer, the term of this patent is extended or adjusted under 35 U.S.C. 154(b) by 144 days.

(21) Appl. No.: 16/468,215

(22) PCT Filed: Nov. 20, 2017

(86) PCT No.: PCT/FR2017/053182
§ 371 (c)(1),
(2) Date: Jun. 10, 2019

(87) PCT Pub. No.: WO2018/104606
PCT Pub. Date: Jun. 14, 2018

(65) Prior Publication Data
US 2020/0009306 A1    Jan. 9, 2020

(30) Foreign Application Priority Data

Dec. 9, 2016    (FR) .................................... 16 62266

(51) Int. Cl.
*A61M 1/10* (2006.01)
*A61M 1/12* (2006.01)
(Continued)

(52) U.S. Cl.
CPC ........ *A61M 60/148* (2021.01); *A61M 60/178* (2021.01); *A61M 60/216* (2021.01);
(Continued)

(58) Field of Classification Search
CPC .............. A61M 60/148; A61M 60/857; A61M 60/865; A61M 60/896; A61M 2205/0266
(Continued)

(56) References Cited

U.S. PATENT DOCUMENTS

2009/0093764 A1    4/2009  Pfeffer
2011/0251450 A1*  10/2011  Pagani ................ A61M 1/3659
                                                             600/16

(Continued)

OTHER PUBLICATIONS

International Search Report, PCT/FR2017/053182, dated Jan. 12, 2018.

*Primary Examiner* — Carl H Layno
*Assistant Examiner* — Jane C Kalinock
(74) *Attorney, Agent, or Firm* — NIXON & VANDERHYE

(57) ABSTRACT

Disclosed is an assembly for fitting/removing a heart pump in a sleeve secured in an opening in a ventricular wall, the assembly including a guide element with a distal end, a proximal end, and a lumen extending between, and opening at, the distal and proximal ends, the heart pump having a pump body. With this pump body including an assembly element, the assembly includes a gripping unit which can slide in the lumen, the gripping unit having at its free end an assembly part which is complementary with the assembly element, which part is configured to cooperate with the assembly element, and to join this free end to the pump body, in order to permit the gripping and displacement of the heart pump.

11 Claims, 5 Drawing Sheets

(51) Int. Cl.
    *A61M 60/148* (2021.01)
    *A61M 60/896* (2021.01)
    *A61M 60/863* (2021.01)
    *A61M 60/216* (2021.01)
    *A61M 60/865* (2021.01)
    *A61M 60/178* (2021.01)

(52) U.S. Cl.
    CPC ........ *A61M 60/863* (2021.01); *A61M 60/865* (2021.01); *A61M 60/896* (2021.01)

(58) Field of Classification Search
    USPC .......................................................... 600/16
    See application file for complete search history.

(56) References Cited

U.S. PATENT DOCUMENTS

| | | | |
|---|---|---|---|
| 2015/0141738 A1* | 5/2015 | Toellner | A61M 60/205 |
| | | | 600/16 |
| 2015/0258260 A1* | 9/2015 | Tuseth | A61M 60/135 |
| | | | 600/16 |
| 2016/0067395 A1* | 3/2016 | Jimenez | A61M 60/178 |
| | | | 606/151 |
| 2016/0121033 A1* | 5/2016 | Cotter | A61M 60/857 |
| | | | 623/3.26 |
| 2016/0175501 A1 | 6/2016 | Schuermann | |
| 2016/0374674 A1* | 12/2016 | Andrus | A61M 60/863 |
| | | | 606/151 |

* cited by examiner

ASSEMBLY FOR FITTING/REMOVING A HEART PUMP

BACKGROUND OF THE INVENTION

Field of the Invention

The present invention relates to an assembly for fitting/removing a heart pump in a sleeve secured in an opening in a ventricular wall.

It also relates to a heart pump for ventricular assistance of a beating heart, this heart pump having a pump body which is configured to cooperate with this assembly for fitting/removing a heart pump, in order to permit gripping and displacement of the pump.

Technological Background

Cardiac insufficiency (CI) is a pathological state in which the heart of the patient is unable to supply a flow of blood necessary for the metabolic needs of the organism.

In order to treat cardiac insufficiency, it is known to implant a ventricular assistance device (VAD), which is an artificial heart pump.

This mechanical pump does not replace the heart, which continues to function, but provides assistance for the weakened ventricle so as to increase the flow of blood in a manner which is adapted to the needs of the individual.

This assistance can be temporary, whilst waiting for a transplant available to carry out a heart transplant.

However, it is found that a significant proportion of patients will not receive such a transplant, either because they are unable to undergo a transplant of this type, for example because of severe cardiac insufficiency, or because no suitable transplant is available for these patients.

In this case, the ventricular assistance is used as the intended purpose, i.e. the artificial heart pump is implanted on a long-term basis.

These heart pumps thus form the subject of intensive research aimed at improving the survival and quality of life of patients with cardiac insufficiency.

Many advances have been made in recent years, and ventricular assistance devices are now known which are more compact, silent, and with an increased service life.

The implantable heart pumps according to the prior art are thus typically equipped with an integrated electric motor in order to ensure their operation, with the speed of rotation of the pump supplying the force necessary to make the blood circulate from the weakened ventricle to the circulation of the body.

Systems are known for implantation of pumps of this type in an orifice in a ventricular wall.

These implantation systems generally comprise a tubular portion, at the ends of which there are placed or formed collars which are each designed to be placed against an opposite face of the ventricular wall, after introduction of the tubular portion into an orifice provided in this ventricular wall.

These collars thus make it possible to retain in position this hollow tubular portion, which then defines an open duct passing through the ventricular wall.

At the end of this tubular portion, which is placed on the exterior of the heart, an aspiration pump is fitted, which ensures the return of the blood which is present in the ventricle, to the circulation of the body.

Although representing a certain amount of progress for the quality of life of patients suffering from cardiac insufficiency, numerous disadvantages are still encountered.

In particular, with these implantation systems according to the prior art, damage caused to the ventricular wall during the installation of the systems is observed, which damage can give rise to local tearing of this wall.

Purely by way of illustration, an implantation system of this type is known, one of the flanges of which is placed against a face of the ventricular wall by means of displacement of the flange along the outer surface of the tubular portion. It is then found that, since the operator cannot control precisely the forces applied on the ventricular wall during the abutment of this flange against the face of the wall, the flange typically compresses the wall and damages it.

In addition, since the dimensions of the flanges are reduced in order to allow them to pass through the orifice, the mechanical strength of the implantation system is limited, and for example does not permit the application of substantial forces on the system once it is in place on the ventricular wall.

Also, since the pump is placed at the end of the tubular portion, on the exterior of the heart, and the blood which is present in the ventricle passes into the open duct, there is a risk of loss of blood, in particular because of the forces applied to the ventricular wall.

Furthermore, since the positioning of the pump relative to the aortic valve is imperfect, the hemodynamic output is not optimized, and the expulsion of the blood is not directed.

Also, the installation and removal and/or replacement of a heart pump of this type are complex, in particular with increased risks of loss of blood.

There is therefore a pressing need not only for a device for securing on an orifice of a ventricular wall, the original design of which overcomes the above-described disadvantages, but also for an assembly for installation/removal or replacement of a heart pump on a securing device of this type.

SUBJECT OF THE INVENTION

The objective of the present invention is to eliminate the disadvantages of the prior art, and to comply with the aforementioned constraints, by proposing in particular an assembly for fitting/removing a heart pump in a duct device which is designed to be placed in a ventricular wall through an opening provided in this wall, this fitting/removing assembly having a particularly simple design and operative mode, which assembly is reliable, and permits firm and secure gripping of this heart pump for the purpose of its manipulation.

Another objective of the present invention is an assembly of this type for fitting/removing a heart pump which permits facilitated maintenance operations on this heart pump, or easy replacement of the pump, whilst the patient's heart continues to beat.

The objective of the present invention is also a heart pump which is especially designed to be implemented with this assembly for fitting/removing a heart pump.

BRIEF DESCRIPTION OF THE INVENTION

For this purpose, the present invention relates to an assembly for fitting/removing a heart pump in a sleeve secured in an opening in a ventricular wall, said assembly comprising a guide element with a distal end, a proximal end, and a lumen extending between, and opening at, said distal and proximal ends, said heart pump having a pump body.

According to the invention, with said pump body comprising an assembly element, said assembly comprises a gripping unit which can slide in said lumen, said gripping unit comprising at its free end an assembly part which is complementary with said assembly element, which part is configured to cooperate with said assembly element, and to join this free end to the pump body, in order to permit the gripping and displacement of said heart pump.

This assembly for fitting/removing a heart pump can advantageously be implemented with any sleeve secured in an opening in a ventricular wall. For example, it is compatible with sleeves according to the prior art, in the form of a hollow duct comprising at each of its ends an element for connection to the ventricular wall.

This gripping unit thus makes it possible to manipulate and displace the heart pump in the lumen of the guide element as far as into the sleeve.

According to different particular embodiments of this fitting/removing assembly, each having its particular advantages and being able to be subjected to numerous possible technical combinations:

- with said assembly element being a hollow, or a projection, provided in or on the pump body, said complementary assembly part is a head with a form paired with said hollow, or respectively a hollow with a form paired with said projection, for assembly of said free end on said pump body;
- the free end of said gripping unit comprises a polygonal profile which is complementary with a hollow profile placed at an end of the heart pump body, such that this free end can be inserted in said hollow profile;
- with said pump body comprising at least two assembly elements, said free end of said gripping unit comprises for each assembly element an assembly part which is complementary with the corresponding assembly element.

These assembly elements, which can or need not be identical, are for example placed on opposite sides of said pump body;

- with said pump body comprising an orifice opening into at least one receptacle for receipt/retention of the pump body, the free end of said gripping unit comprises a head which is maneuverable in rotation, which head has one or a plurality of indexing reliefs defining, by rotation of the head, an unlocked position of the pump body and of the end of the gripping unit, in order to permit their separation, said head being able to pass freely through said orifice in order to penetrate into, or exit from, said receptacle, and a locked position, in which the indexing relief(s) is/are engaged in the receipt/retention receptacle in order to provide mechanical assembly of said end of the gripping unit and said heart pump;
- said gripping unit is an elongate body with a generally cylindrical form, such that it can be rotated in the lumen of said guide element.

Purely by way of illustration, this rotation of the gripping unit can be used to screw/unscrew said pump body on said thread supported by the inner wall of said sleeve;

- this fitting/removing assembly comprises a sealing element placed inside said lumen, and preferably in its distal part, this sealing element being open when the free end of said gripping unit is pressed against it, in order to open up the passage for said gripping unit through this sealing element;
- the distal end of said guide element comprises a device for stabilization of part of the heart, said stabilization device comprising a widened part, which preferably comprises at its end with the widest diameter a groove which has at least one aspiration orifice for creation of a vacuum in said groove when a portion of the ventricular wall is in contact with said stabilization device;
- this fitting/removing assembly comprises one or a plurality of other elements selected from the group comprising a perforation tool, a dilator tool, a guide wire, etc., and combinations of these elements, each of said elements or their combinations being able to slide in said lumen.

The present invention also relates to a heart pump for ventricular assistance for a beating heart, said heart pump having a pump body.

According to the invention, the pump body comprises at least one assembly element which is configured to cooperate with the free end of the gripping unit of said assembly for fitting/removing a heart pump as previously described, in order to permit the gripping and displacement of said heart pump.

This pump is thus especially designed to be implemented with the fitting/removing device previously described. It therefore has a connection to this fitting/removing assembly, and is designed to function therewith.

According to different particular embodiments of this heart pump, each having its particular advantages and being able to be subjected to numerous possible technical combinations:

- this pump is a propulsive heart pump;
- with said sleeve extending in an axial direction and comprising a front axial end and a rear axial end, said sleeve comprising an inner channel which opens at the front and rear axial ends, at least part of the inner wall of said sleeve delimiting said inner channel having a thread, said pump body comprising a thread on part of its outer surface, which is distinct from said at least one assembly element, said thread being complementary with the thread of said at least part of the inner wall of the sleeve in order to ensure their engagement.

Preferably, these threads are configured to ensure the sealing of the pump body/sleeve assembly.

Alternatively, with said sleeve extending in an axial direction and comprising a front axial end and a rear axial end, said sleeve comprising an inner channel which opens at the front and rear axial ends, the inner wall of said sleeve delimiting said inner channel comprises at least two means for snapping-in, said pump body comprising for each means for snapping-in of the sleeve a complementary means for snapping-in, which is configured to cooperate with a corresponding means for snapping-in of the sleeve in order to ensure the assembly of the pump body on the inner wall of the sleeve, each complementary means for snapping-in being placed on the outer surface of the pump body, whilst being distinct from said at least one assembly element.

Preferably, said pump body has a peripheral seal placed upstream from the means for snapping-in, in order to ensure the sealing of the pump body/sleeve assembly.

Upstream relates to the direction of flow which the blood exiting from the heart through the sleeve would have.

The present invention also relates to a device for securing on an opening in a ventricular wall, comprising:

- a hollow main body with a generally cylindrical form with an outer surface;

a ring which is received at a first end of said hollow body, this ring being mobile along at least part of the outer surface of the hollow body;

a tubular membrane covering the outer surface of the outer body, whilst extending between said ring and the end opposite the first end of the hollow body, known as the second end;

a distal end of this tubular membrane, placed on the side of said second end of the hollow body, being self-expandable between a first stable configuration in which it has a tubular or substantially tubular form, and a second stable configuration in which it defines a first flange extending radially, or substantially radially, starting from said hollow body, this first flange being designed to abut a face of said ventricular wall;

the other end, known as the proximal end, of this tubular membrane being able to be deformed by the displacement of said ring along the outer surface of the hollow body, such as to form a retention flange, the position of which can vary relative to said first flange, so as to adapt to ventricular walls with different thicknesses;

said retention flange being designed to come into contact with the opposite face of said ventricular wall, such that said flanges and the assembly formed by the part of the hollow body and the portion of the tubular membrane covering it, passing through said ventricular wall through said opening, lock said securing device in position in said opening.

This ring, known as a pressing ring, has a form suitable for engaging on the outer surface of said hollow body. It is placed at, or in the vicinity of, said first end of the hollow body.

Advantageously, this ring makes it possible to compress the tubular membrane placed on the outer surface of said hollow body. The degree of compression, or pressing, of the tubular membrane, is controlled by the operator by displacing the ring to a greater or lesser extent along the outer surface of the hollow body. The forces applied on the ventricular wall are thus advantageously controlled.

For this purpose, on its edge which is designed to come into contact with the proximal end of said tubular membrane, the ring has an annular surface for pressing said tubular membrane. This annular surface can comprise a receptacle for receipt of the proximal end of the tubular membrane.

The proximal end of the tubular membrane can thus be deformed by widening towards the exterior such as to form a retention flange spaced from the first flange. This radially widened flange advantageously has a planar or substantially planar surface which is designed to face the ventricular wall.

The hollow body has a longitudinal dimension larger than that of the opening extending between the opposite faces of the ventricular wall, and a diameter which is the same as, or larger than, that of the opening in the ventricular wall.

Thus, and advantageously, the device for securing on an opening in a ventricular wall ensures sealing after being fitted, without any suture being performed, contrary to the devices of the prior art. In this respect, the device in question is for fixing a ventricular puncture with a diameter larger than 20 mm, which does not require any stitch.

In different particular embodiments of this device, each having its particular advantages and being able to be subjected to numerous possible technical combinations:

the proximal end of the tubular membrane is configured to be deformed progressively during the displacement of the ring, such as to form a retention flange, the position of which can vary within a predetermined range of distances starting from the first flange;

said ring comprises on its periphery at least one coupling finger which is designed to cooperate with notches placed in the outer surface of said hollow body.

This therefore results in discrete or intermittent displacement of the ring along the outer surface of the hollow body.

Alternatively, with the outer surface of said hollow body comprising a thread on at least part of its outer surface, the inner surface of said ring comprises a thread which is configured to cooperate with said thread placed on the outer surface of the hollow body, in order to permit the displacement of said ring;

said ring comprises a non-return finger in order to prevent any loosening of the ring after formation of the retention flange;

the outer surface of the hollow body comprises a stop in order to prevent the displacement of said ring;

said ring and said hollow body are made of rigid materials which are inert for the human body;

said tubular membrane is made of nitinol, of a nitinol alloy, or also of expandable polyurethane;

the device is configured to form a retention flange with an outer diameter which is strictly larger than 3/2 D, where D is the diameter of the opening in the ventricular wall.

Preferably, the retention flange thus formed has an outer diameter of between 3/2 D and 3 D.

Purely by way of illustration, this retention flange has a diameter of 40 mm. This large dimension of the retention flange designed to be formed thus reinforces the support of the device on the ventricular wall, and consequently ensures better retention in position, or stabilization, of the securing device on this ventricular wall, in particular during intervention on the propulsive heart pump which is designed to be received in the channel of this main body.

Furthermore, any stresses are distributed over a larger surface area of the ventricular wall, such that the risk of damaging this wall is reduced, or even eliminated;

with the inner wall of the hollow body delimiting a channel extending between the first and second ends of the hollow body, said inner wall comprises means for sealed assembly of the body of a heart pump and said wall, said heart pump thus being received at least partly in said channel. The diameter of the channel is equal, or substantially equal, to the outer diameter of the body of the pump, in order to accommodate the pump in said channel.

Preferably, with the body of the pump which is designed to be accommodated in the channel delimited by the inner wall of the hollow body comprising a thread on its outer surface, this inner wall comprises a thread which is designed to cooperate with the thread of the pump body;

said heart pump is an implantable ventricular assistance device (VAD).

Preferably, it is a propulsive heart pump.

With this heart pump being anchored to the wall of the heart by means of the securing device, the patient can thus move actively without any risk.

The first end of the hollow main body comprises an opening which is in communication with the channel delimited by the inner wall of the hollow body. Advantageously, one or a plurality of wired connections such as wires can pass through this opening in order to connect an artificial heart pump accommodated in this channel to a control unit of this pump. Signals for control of this pump can thus be sent to the artificial pump.

This control unit can also comprise a wireless emitter-receiver to transmit automatically data such as information on the rate of heartbeat or the state of the supply source implanted, for the purpose of remote medical monitoring.

Data can be transmitted to a portable external terminal by means of short-range wireless communication signals, for example based on a Bluetooth or Zigbee protocol, etc. This external terminal can comprise a means for communication which implements a cellular access network and/or an Internet network, in order to transmit this data to a cardiologist for example. The cellular access network can be of several types (2G, 3G, 4G), with each type of network being accessible according to a plurality of cellular access technologies (2G: EDGE, GPRS, 3G: UMTS, HSDPA, HSUPA, HSPA, HSPA+, 4G: LTE). The Internet network is for example a network comprising wireless non-cellular access points such as a WLAN network, for example Wi-Fi or WiMAX or also a Li-Fi network. This external terminal can have a display device in order to allow the user to read messages or choose options from a menu.

Preferably, this central unit comprises one or a plurality of inputs for receipt of one or a plurality of signals, each of which is associated with an audible or inaudible mechanical vibration associated with the mechanical activity of the heart, said central unit comprising a first sub-set of software instructions of said set of software instructions which, when they are executed by said processor, are configured to define a temporal window for measurement of said signal(s) in order to analyze each signal thus received at the input of said central unit during this temporal window, so as to determine one or a plurality of parameters of the corresponding signal, in order to compare the parameter(s) of each signal thus determined with one of a plurality of items of data previously recorded in a storage unit of said central unit, so as to identify the signal corresponding to the closure of the mitral valve, as well as the instant $t_1$ corresponding to the closure of said mitral valve.

The present invention also relates to a ventricular assistance unit comprising a propulsive heart pump and a device for securing on an opening in a ventricular wall, as previously described.

Advantageously, this propulsive heart pump is accommodated inside the channel delimited by the inner wall of the hollow main body. Preferably, the pump body and the inner wall of the hollow main body are assembled in a sealed manner so as to prevent any reflux of blood.

BRIEF DESCRIPTION OF THE DRAWINGS

Other advantages, objectives and particular characteristics of the present invention will become apparent from the following description, provided by way of explanation which is in no way limiting, with reference to the appended drawings in which.

DETAILED DESCRIPTION OF AN EMBODIMENT OF THE INVENTION

Figure 1:
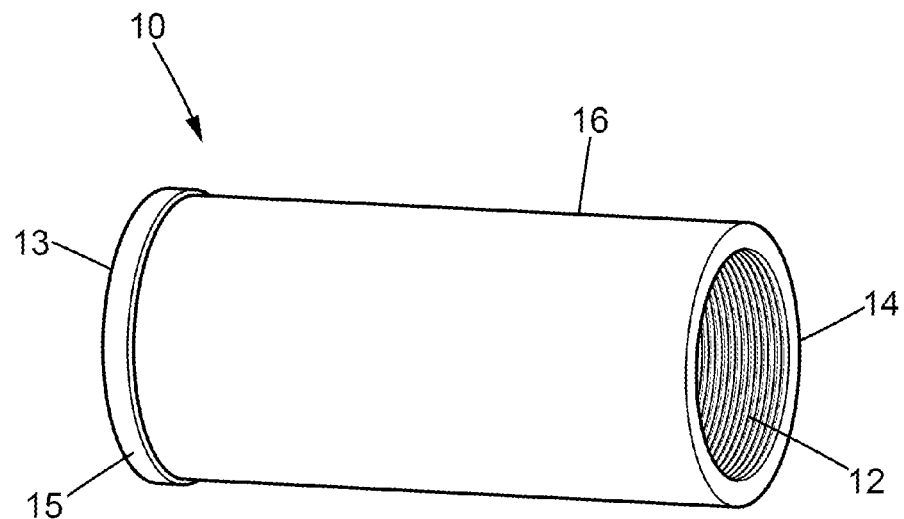
FIG. 1 represents schematically a device for anchorage without suture for a propulsive heart pump according to a particular embodiment of the invention, the distal end of the tubular membrane being in its first stable configuration, and the ring not yet having been displaced along the outer surface of the tube, in order to compress the proximal end of the tubular membrane.
Figure 2:
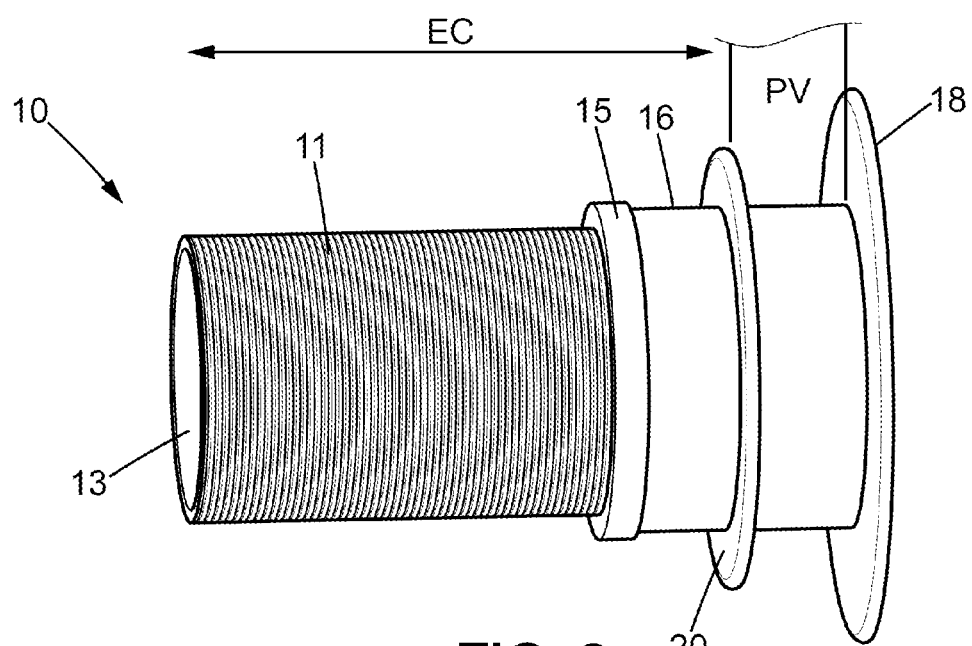
FIG. 2 shows the anchorage device in FIG. 1 in an activated state, in which the distal end of the tubular membrane is in its second stable configuration, and the proximal end of the tubular membrane has been deformed in order to define a retention flange; the opposite faces of a ventricular wall (PV) have been schematized in the upper part of the device in order to illustrate the putting into contact of the flanges on these opposite faces, with the extra-cardiac space (EC) also being shown.
Figure 3:
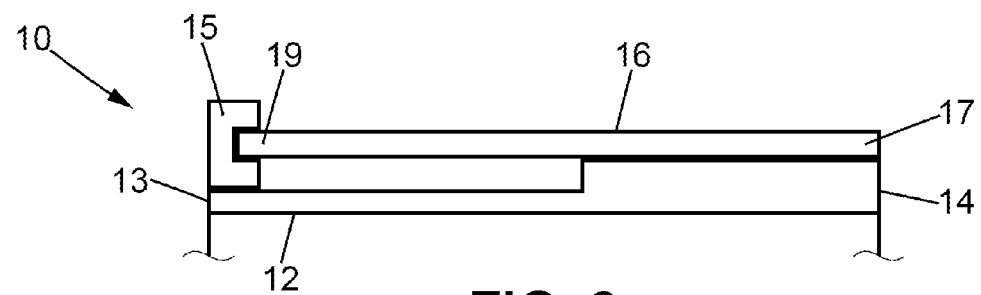
FIG. 3 is a partial schematic representation in cross-section of the anchorage device illustrated in FIG. 1.
Figure 4:
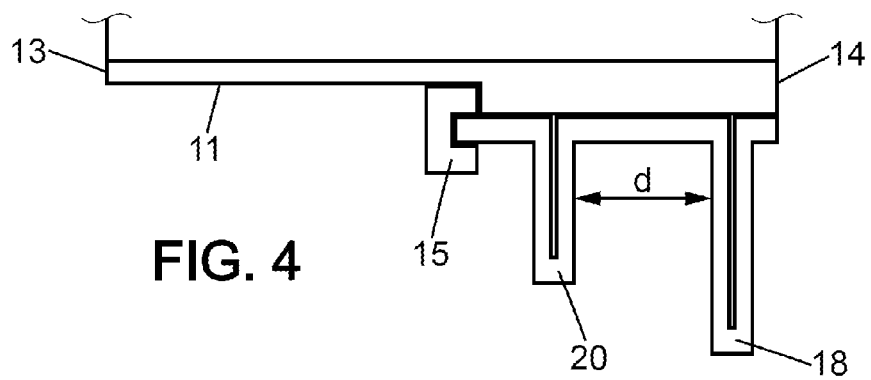
FIG. 4 is a partial schematic representation in cross-section of the anchorage device illustrated in FIG. 2.
Figure 5:
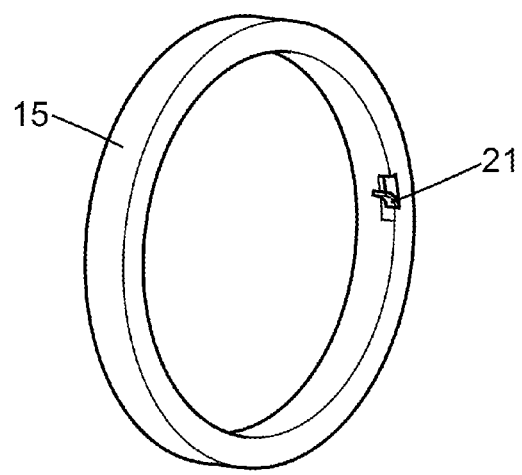
FIG. 5 is a view in perspective of the ring of the anchorage device in FIG. 1, showing the non-return valve of the ring.
Figure 6:
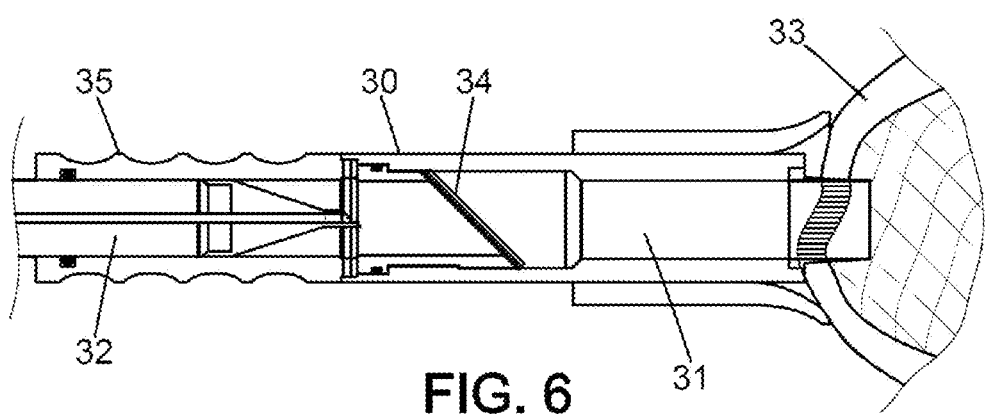
FIG. 6 is a view in longitudinal cross-section of a fitting/removing assembly of a heart pump connected to the apex of a beating heart, according to a particular embodiment of the invention, this assembly being shown in a first configuration in which it comprises a tool for perforation and ablation of part of the ventricular wall, in order to create an opening in said wall for the purpose of placing a sleeve in this opening.
Figure 7:
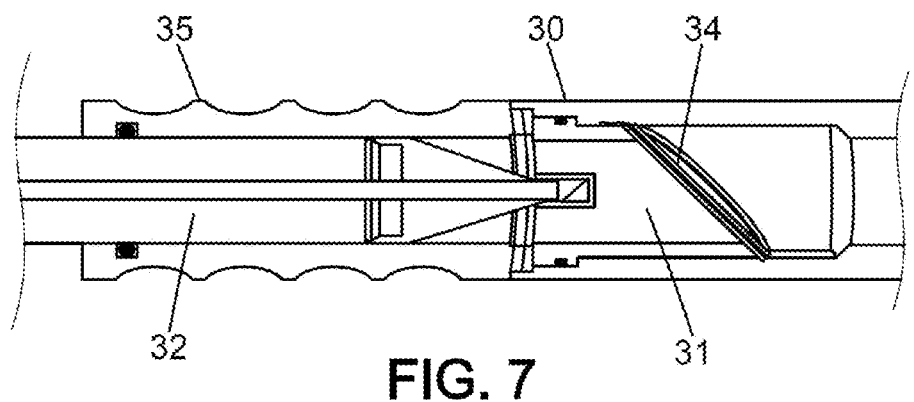
FIG. 7 is an enlarged view in longitudinal cross-section of the fitting/removing assembly in FIG. 6, with the end of the perforation and ablation tool comprising a cap to protect its needle before passage through the flap valve.
Figure 8:
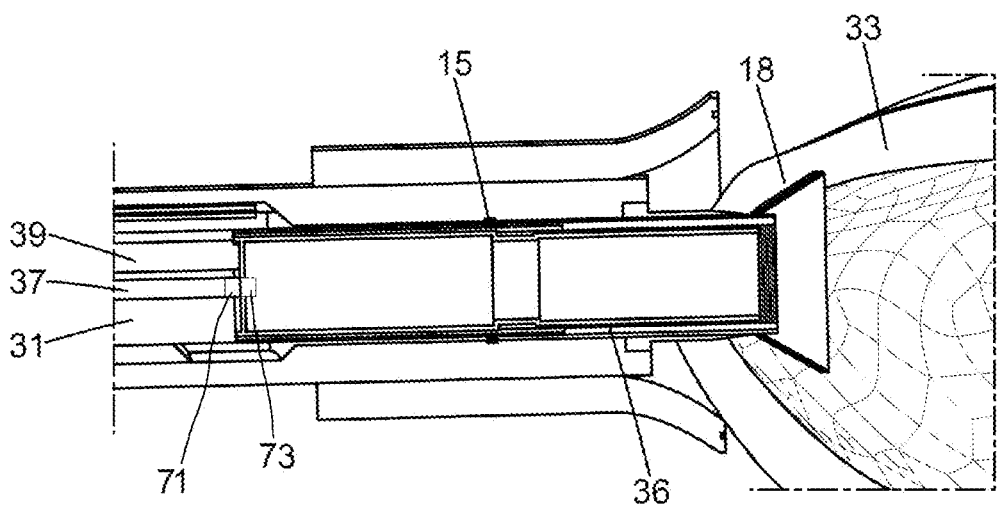
FIG. 8 is a partial view in longitudinal cross-section of the fitting/removing assembly in FIG. 6 according to another configuration, in which this assembly comprises a gripping unit, the end of which is connected to a heart pump engaged in an anchorage device placed in the opening in a ventricular wall, and passing through this wall, the distal end of the tubular membrane being in its second configuration.
Figure 9:
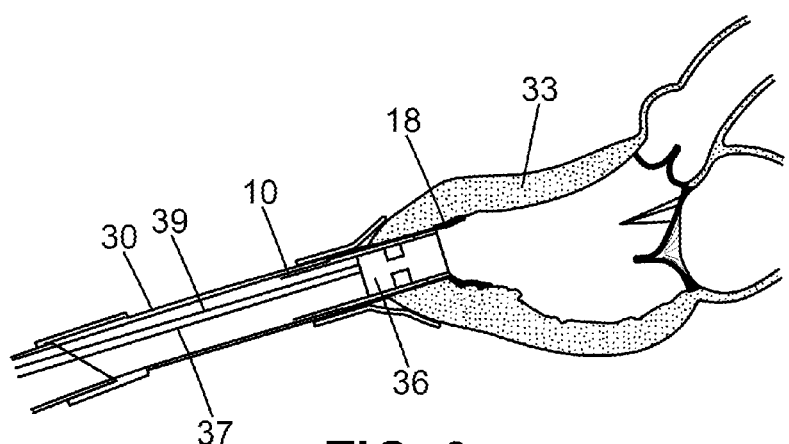
FIG. 9 is another representation of the fitting/removing assembly in its configuration illustrated in FIG. 8, also showing the deployment of the distal end of the tubular membrane inside the apex.
Figure 10:
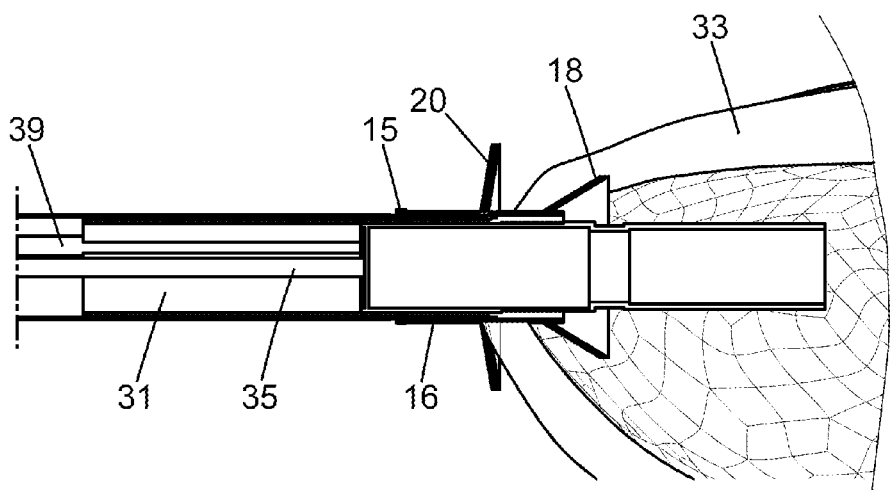
FIG. 10 is a view in longitudinal cross-section of the fitting/removing assembly of a heart pump in FIG. 8, in which the ring for compression of the tubular membrane has been displaced along the outer surface of the tube, in order to form a retention flange, the anchorage device thus being secured in the opening in the ventricular wall, and part of the heart pump being intraventricular.
Figure 11:
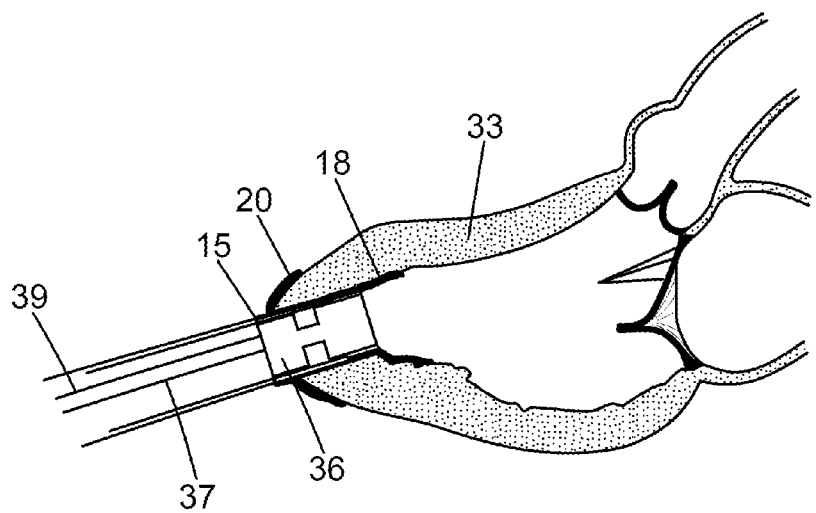
FIG. 11 is another representation of the fitting/removing assembly in its configuration illustrated in FIG. 10, also showing the deployment of the proximal end of the tubular membrane on the outer surface of the apex.
Figure 12:
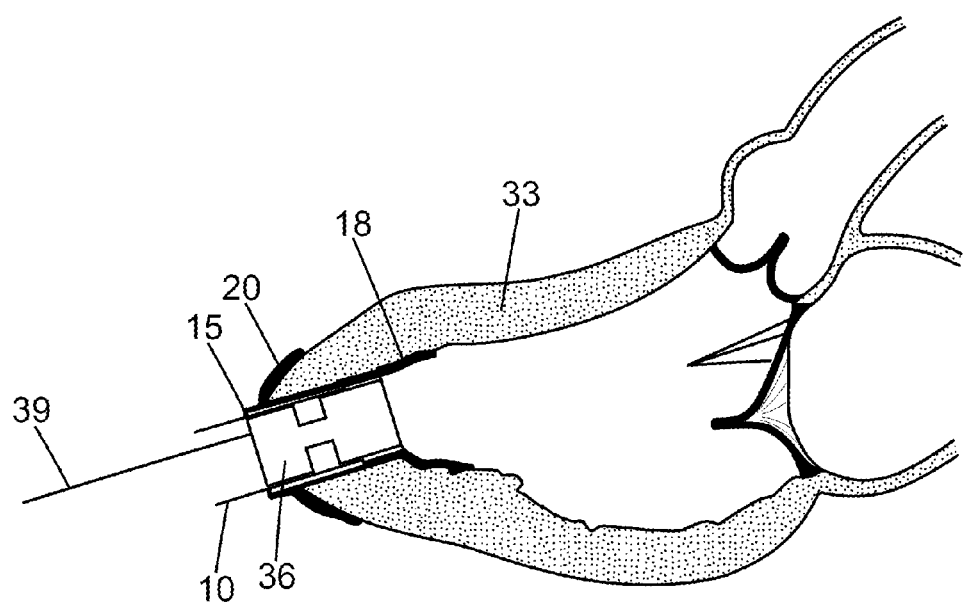
FIG. 12 shows the anchorage device secured in the opening in the ventricular wall, the pump being screwed into the inner channel of this anchorage device, the fitting/removing assembly having been removed.

Firstly, it should be noted that the figures are not to scale.

FIGS. 1 to 5 show schematically a device 10 for anchorage without suture of a propulsive heart pump in an opening in a ventricular wall, according to a particular embodiment of the present invention.

This anchorage device 10 comprises a tube with an outer surface 11 and an inner surface 12 delimiting a channel extending between a first end 13 and a second end 14 of this tube, which ends are open.

The outer 11 and inner 12 surfaces of this tube 10 have a thread, the outer surface 11 of the tube comprising on the side of its second end 14 a portion of wall with an excess thickness which is not threaded, and is connected by a shoulder to the remainder of the outer surface 11 of the threaded tube. This shoulder thus defines a stop in order to limit the displacement of a pressing ring 15 received at the first end 13 of the tube.

The inner surface of this ring 15 comprises a thread (not represented) which is designed to cooperate with the thread of the outer surface 11 of the tube, in order to permit continuous displacement of this ring 15 along part of the outer surface 11 of this tube.

Between this ring 15 and the second end 14 of the tube, a tubular membrane 16 is placed, which covers the outer surface 11 of the tube.

The ring 15 comprises on its face which is designed to press the tubular membrane 16 a receptacle such as a groove, in order to receive the corresponding free end of the tubular membrane 16. Advantageously, this end of the tubular membrane 16, which is also known as the proximal end, is not rendered integral in its receptacle in order to prevent torsions of the membrane.

A distal end 17 of this tubular membrane 16, placed on the side of the second end 14 of the tube, is self-expandable between a first stable configuration in which it has a tubular form, and a second stable configuration in which it defines a first flange 18 extending radially from said tube.

The first stable configuration of the membrane advantageously permits easy introduction of the second end 14 of the tube through the opening in the ventricular wall.

The second stable configuration of the tubular membrane 16 makes it possible to generate a first flange 18, such that the flange abuts, or is placed against, a face of the ventricular wall, when the tube has been introduced through the opening in this ventricular wall.

The transition from the first stable configuration to the second stable configuration is obtained by means of an increase in the temperature of the tubular membrane 16, for example by exposing it to the temperature of the human body, the tubular membrane 16 being made of nitinol or expanded polyurethane, which is a form memory material.

The opposite end, known as the proximal end 19, of this tubular membrane 16, is able to be deformed progressively by the displacement of the ring 15 along the outer surface 11 of the tube, such as to form a second retention flange 20, the position of which can vary within a predetermined range of distances d starting from the first flange 18 defined by the distal end 17 of the tubular membrane 16 in its second stable configuration. This distance d makes it possible to compress the ventricular wall in order to ensure the sealing of the device, as well as reliable and durable retention.

It is thus possible to adapt the anchorage device 10 to ventricular walls with different thicknesses. The shoulder determined by the profile of the outer surface 11 of the tube advantageously makes it possible to define an upper limit for the compression of the tubular membrane 16, and thus to limit the forces applied on the ventricular wall.

Advantageously, this ring 15 comprises a non-return finger 21.

This non-return finger 21 makes it possible to prevent any loosening of the ring 15 after formation of the second retention flange 20, which would be liable to give rise to release, or partial release, from the stresses in the tubular membrane 16, with the consequence of subsidence of the second retention flange 20. Deformation of this type of the second retention flange 20 would be liable to give rise to poorer sealing of the connection between the anchorage device and the ventricular wall, which would be liable to result in leakages of blood.

The ring 15 and the tube are made of rigid, inert materials, i.e. which are biocompatible with the human organism. They are for example made of PEEK (polyetheretherketone), of ceramic or of titanium. These elements can be printed, i.e. they are then formed by a three-dimensional printing process.

Once this anchorage device 10 has been rendered integral with the ventricular wall, it is possible to introduce a propulsive heart pump into the channel delimited by the inner surface 12 of the tube.

This pump (not represented) is advantageously designed to be received in the channel of the tube, such that it does not form a projection from the tube outside the heart.

In addition, the assembly of the pump body and the inner surface 12 of the tube is sealed in order to prevent any reflux of blood via this channel. An assembly of this type is advantageously formed in this case by screwing the pump body onto the thread supported by the inner surface 12 of the tube.

For this purpose, the pump body has on at least part of its outer surface 11 a thread which is designed to cooperate with the thread supported by the inner surface 12 of the tube.

The screwing of the pump into the inner surface 12 of the tube also makes it possible to regulate or adjust the positioning of this pump relative to the aortic valve, and consequently to optimize the position of the pump so as to obtain a better hemodynamic performance. Advantageously, this therefore provides an optimized cardiac output, which is made possible by the possibility of creating continuous, and consequently extremely precise, displacement of the pump body along the thread formed on the inner surface 12 of the tube.

Thus, and more generally, the present invention also relates to a method designed to optimize the hemodynamic performance, wherein there is adjustment of the position of a heart pump implanted on a ventricular wall relative to the aortic valve of the patient. Preferably, this adjustment is obtained by a displacement of the heart pump relative to this aortic valve. More preferably, this adjustment is carried out by screwing/unscrewing the body of the pump along a threaded inner surface, or on the threaded inner side, of a tubular wall of a securing or anchorage device secured in an opening in a ventricular wall, the pump body comprising for this purpose on its outer surface a thread which is complementary with the thread of the threaded inner side of the tubular wall, and is designed to cooperate with the latter. An adjustment of the position of this type is advantageously very precise because of the continuous displacement of the heart pump permitted by these threads.

The objective is thus to position the end of the heart pump in order to direct the blood propelled by this pump to the aortic valve of the patient. Preferably, the objective is to place this end of the heart pump at a distance of between 10 mm and 20 mm from the aortic valve.

In order to limit the displacement of the heart pump by screwing the pump along the inner surface 12 of the tube, this inner surface 12 of the tube can comprise at least one stop. It is thus possible to control the intraventricular advance of the heart pump.

FIGS. 6 to 13 illustrate a system for introduction of a medical device such as a needle, a device 10 for anchorage on an orifice in a ventricular wall as described above, a heart pump, or also a unit for gripping this pump, according to a particular embodiment of the present invention.

This system for the introduction of a medical device comprises a main body 30 defining a longitudinal inner channel or lumen 31 for receipt of this medical device 32, this medical device being mobile in translation in this inner channel 31, such that a part of it can be placed projecting from this main body 30, for its introduction into a ventricular wall 33 or into the channel delimited by the inner wall 12 of a sleeve secured in the opening in the ventricular wall 33, such as that of an anchorage device described above.

This main body 30 also comprises a sealing element 34, which is placed inside this channel, such that this sealing element 34 can be open when the end of the medical device is pressed against it, in order to open up the passage for the medical device 32 through this sealing element 34.

In this case, this sealing element 34 comprises a valve, the seat of which is inclined by 45° in order to facilitate the passage of the medical device 32, whilst preventing the passage of the blood in the other direction when this flap valve is in its closure position. This flap valve thus forms a non-return valve.

The proximal end of the main body 30 comprises a gripping handle 35, and the distal end of the main body advantageously comprises a venting valve (not represented) in order to eliminate the presence of any air in the part of the inner channel positioned downstream from the sealing element 34.

In order to manipulate the heart pump 36 for its implantation in, or its removal from, the channel delimited by the inner wall 12 of the tube, this system comprises a gripping unit 37 which can slide in the inner channel 31, this gripping unit 37 having at its free end a part 71 which is complementary with a recess 73 contained in the pump body.

It is thus possible to ensure the engagement of the free end of this gripping unit 37 and the recess in the pump body, for gripping and manipulation of the heart pump 36.

Purely by way of illustration, with the pump body having a hollow polygonal recess such as one with six facets provided in a hollow in the pump body, the free end of the gripping unit 37 has a complementary form, such as a male hexagon form. This gripping unit 37 is advantageously in the form of a rod which the operator can manipulate by means of its proximal end, such as to rotate the rod in order to screw or unscrew the pump body in its receptacle defined by the channel delimited by the inner wall 12 of the tube.

Figure 13:
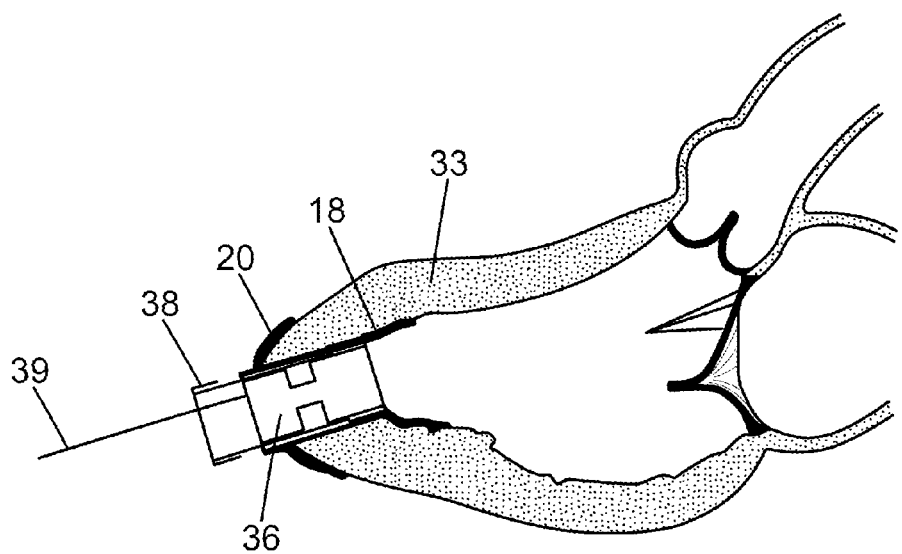
FIG. 13 shows the anchorage device secured in the opening in the ventricular wall, the pump being screwed in the inner channel of this anchorage device, a stopper being placed at the end of the anchorage device which is placed outside the heart in order to close the end, this stopper comprising an orifice for the passage of the heart pump supply.

FIG. 13 shows the anchorage device secured in the opening in the ventricular wall, the heart pump 36 being screwed into the inner channel of this anchorage device, a stopper 38 being placed at the end of the anchorage device which is placed outside the heart in order to close this end, this stopper 38 comprising an orifice for the supply passage 39 of the heart pump 36.

The invention claimed is:

1. An assembly for fitting/removing a propulsive heart pump (36) in a sleeve secured in an opening in a ventricular wall (33), said assembly comprising:
   an assembly element of a pump body of the heart pump (36);
   a guide element (30) with a distal end, a proximal end, and a lumen (31) extending between, and opening at, said distal and proximal ends; and
   a gripping unit (37) configured to slide in said lumen (31), a free end of said gripping unit (37) comprising an assembly part which is complementary with said assembly element of the pump body,
   said assembly part of said gripping unit (37) configured to cooperate with said assembly element to present two positions that include i) a locked position in which said gripping unit (37) is mechanically joined to the pump body wherein the gripping unit (37) grips the pump body in order to displace the heart pump (36), and ii) an unlocked position with respect to the pump body wherein said free end is separable from the pump body.

2. The assembly as claimed in claim 1, wherein, with said assembly element being a hollow, or a projection, provided in or on the pump body, said assembly part is a head with a form paired with said hollow, or respectively a hollow with a form paired with said projection, for assembly of said free end on said pump body.

3. The assembly as claimed in claim 2, further comprising:
   a sealing element located inside a distal part of said lumen (31), the sealing element being open when the free end of said gripping unit (37) is pressed against the sealing element in order to open the passage for said gripping unit (37) through the sealing element.

4. The assembly as claimed in claim 2, wherein the distal end of said guide element (30) comprises a stabilization device comprising a widened part that widens progressively, a terminal end of said widened part having a widest diameter and a groove in a surface thereof to engage with a portion of the ventricular wall (33).

5. The assembly as claimed in claim 1,
   wherein said pump body includes an orifice opening into a recess in the pump body, and
   wherein the assembly part of the free end of said gripping unit (37) is a head which is maneuverable in rotation, the head being configured to cooperate with the recess of the pump body so that, in the locked position, the head engages with said heart pump (36) inside the recess, and in the unlocked position, the head is able to pass freely through said orifice of the pump body in order to penetrate into or exit from said recess.

6. The assembly as claimed in claim 1, wherein said gripping unit (37) is an elongate body with a cylindrical form, such that the gripping unit is rotatable in the lumen (31) of said guide element (30).

7. The assembly as claimed in claim 1, further comprising:
   a sealing element placed inside said lumen (31), the sealing element being open when the free end of said gripping unit (37) is pressed against the sealing element in order to open a passage for said gripping unit (37) through the sealing element.

8. The assembly as claimed in claim 1, wherein the distal end of said guide element (30) comprises a stabilization device comprising a widened part that widens progressively, a terminal end of said widened part with a widest diameter having a groove in a surface thereof to engage with a portion of the ventricular wall (33).

9. The assembly as claimed in claim 1, further comprising:
   one or more elements selected from the group consisting of: a perforation tool, a dilator tool, and a guide wire, each of said elements being able to slide in said lumen (31).

10. The assembly as claimed in claim 1, said sleeve (10) comprising an inner channel and said heart pump being configured to be received in the channel of said sleeve, said sleeve (10) extending in an axial direction and further comprising a front axial end (14) and a rear axial end (13), said inner channel opening at the front and rear axial ends, at least part of an inner wall of said sleeve (10) delimiting said inner channel having a first thread, and said pump body comprising a second thread on part of an outer surface of said pump body which is distinct from said at least one assembly element, said second thread being complementary with the first thread of said at least part of the inner wall of the sleeve (10) in order to ensure engagement between the sleeve (10) and the pump body.

11. The assembly as claimed in claim 10, wherein said first and second threads are configured to ensure sealing of the pump body to the sleeve.

\* \* \* \* \*